United States Patent [19]
Morlotti

[11] Patent Number: 5,272,088
[45] Date of Patent: Dec. 21, 1993

[54] METHOD AND APPARATUS FOR DETECTING THE PRESENCE OF CARBON DIOXIDE IN A SAMPLE

[75] Inventor: Romano Morlotti, Varazze, Italy

[73] Assignee: Minnesota Mining and Manufacturing Company, St. Paul, Minn.

[21] Appl. No.: 52,286

[22] Filed: Apr. 26, 1993

Related U.S. Application Data

[63] Continuation of Ser. No. 929,672, Aug. 13, 1992, abandoned.

[30] Foreign Application Priority Data

Sep. 12, 1991 [IT] Italy ................... A002412

[51] Int. Cl.$^5$ ................ G01N 33/50; H01L 21/306; F21V 9/16
[52] U.S. Cl. .................... 436/68; 436/127; 436/133; 436/172; 250/367; 250/368; 250/459.1
[58] Field of Search .............. 436/68, 127, 133; 435/172; 356/39; 250/367, 368, 459.1; 128/633

[56] References Cited

U.S. PATENT DOCUMENTS

| | | | |
|---|---|---|---|
| 4,251,750 | 2/1981 | Gallien et al. | 356/39 |
| 4,534,884 | 8/1985 | Arakawa et al. | 252/301.4 |
| 4,861,727 | 8/1989 | Havenstein et al. | 436/136 |
| 4,925,268 | 5/1990 | Iyer et al. | 422/82.06 |
| 5,045,707 | 9/1991 | Chakrabarti et al. | 250/484.1 |
| 5,049,779 | 9/1991 | Itsuki et al. | 313/486 |

FOREIGN PATENT DOCUMENTS

| | | |
|---|---|---|
| 0105870 | 4/1984 | European Pat. Off. |
| 0320768 | 6/1989 | European Pat. Off. |
| 0391153 | 10/1990 | European Pat. Off. |

OTHER PUBLICATIONS

Database WPIL, Week 8426, Derwent Publications Ltd., London, GB; AN 84-161903 and JP-59 086 684 (Fuji Photo Film KK) May 18, 1984.

Gehrich et al., IEEE Trans. on Biomedical Engineering, vol. BME-33, No. 2, pp. 117-132, Feb. 1986.

Ishihara et al., Journal of Electrochem. Soc., vol. 138, No. 1, Jan. 1991.

Rosenblatt et al., Physical Review B., vol. 39, No. 14, pp. 10209-10218, May, 1989.

Anpo et al., J. Chem. Soc., Faraday Trans I, 84(3), pp. 751-764, (1988).

Amigues et al., Disc. Faraday Soc., 41, pp. 362-379 (1966).

Thornton et al., J. Chem. Soc. Faraday Trans. I, vol. 71, pp. 461-472 (1975).

Lunsford et al., J. Phys. Chem., 69(7), pp. 2182-2184 (1965).

*Primary Examiner*—James C. Housel
*Assistant Examiner*—N. Bhat
*Attorney, Agent, or Firm*—Gary L. Griswold; Walter N. Kirn; John H. Hornickel

[57] ABSTRACT

Europium activated magnesium oxide phosphors are described as useful photoluminescent materials, to be used in methods for detecting the presence or determining the concentration of carbon dioxide in a sample, comprising the steps of a) exposing to a predetermined wavelength range radiation a carbon dioxide-quenchable photoluminescent phosphor put in contact with the sample to cause the phosphor to store energy radiation, b) stimulating the photoluminescent phosphor with infrared radiation to release the stored energy as photoluminescent light, c) detecting and measuring the intensity of said photoluminescent light and d) correlating the measured intensity with an intensity of the photoluminescent light previously measured at a given reference carbon dioxide pressure value.

6 Claims, 1 Drawing Sheet

METHOD AND APPARATUS FOR DETECTING THE PRESENCE OF CARBON DIOXIDE IN A SAMPLE

This is a continuation of application Ser. No. 07/929,672 filed Aug. 13, 1992, now abandoned.

FIELD OF THE INVENTION

The invention relates to a method and an apparatus for detecting the presence or determining the concentration of carbon dioxide gas in a sample, more preferably to a method and an apparatus for detecting the presence or determining the concentration of carbon dioxide in blood by stimulating a photoluminescent phosphor.

BACKGROUND OF THE ART

In many cases it is useful to know if a gaseous compound is present in a sample and to determine its concentration. The medical field is the most important sector where such information can be very useful. In fact a blood gas analysis is performed on many hospital patients both during and after surgery. Three parameters of interest in the blood analysis are the partial pressures of oxygen ($pO_2$) and carbon dioxide ($pCO_2$) and the negative logarithm of hydrogen ion activity (the pH).

Other fields in which this kind of information can be applied are industrial processes wherein a gas container is involved: for example, an oil containing tank, a container wherein some chemical reactions occur, a fermentation process for the production of food, and the like.

Additional fields of application also can be considered. For example, it could be useful to know about the oxygen or carbon dioxide gas presence when mining in a tunnel, or when operating in any underground areas. This advances the safety of people who have to work for many hours in such environmental conditions.

In the medical field, luminescent aromatic molecules have been found useful to detect the oxygen presence or the carbon dioxide presence in blood samples. These molecules are not in direct contact with the liquid medium, i.e. blood, but they are separated by a polymeric membrane permeable to oxygen molecules and not permeable to water molecules. In such a way the $pO_2$ and the $pCO_2$ at the luminescent molecules interface are, respectively, proportional to the concentration of the oxygen and of carbon dioxide in blood. For that reason, the suitability of a sensor to detect $pO_2$ or $pCO_2$ changes can be assessed separately, in a gaseous atmosphere simulating that in equilibrium with blood.

Generally the presence of carbon dioxide in a sample, for example, blood, is performed by fiber optic fluorescent sensors having a pH sensitive dye which detects changes in hydrogen ion concentration in a bicarbonate containing solution, which in turn varies as a function of the level of carbon dioxide present in the blood according to the mass action law (see Gehrich et al., IEEE Trans. on Biomedical Engineering, Vol. BME-33, No. 2, pp. 117–132, February 1986). By this way, the presence of carbon dioxide is not measured in a direct way, but as a consequence of the level of pH present in the sample. These kinds of measuring systems can determine some mistakes and sometimes the data obtained are not very precise. It could be useful to have a method which directly supply the carbon dioxide values in the sample, without measuring the pH level.

Additional methods to monitor carbon dioxide concentration in a sample are performed by using solid electrochemical cells, or by using calorimetric cells based on calcium ion-exchanged A-type zeolite and on carbonation of hydroxyapatite, respectively, or by using electrical resistence change associated to the electrochemical reduction of $CO_2$, or by using oxide capacitors consisting of mixtures of $BaTiO_3$ with oxides such as PbO, CuO, NiO (see Ishihara et al., Journal of Electroch. Soc., Vol. 138-1, 173, 1991).

All such methods to monitor carbon dioxide are not always satisfactory with respect to sensitivity and long term stability. Such methods may often require high working temperature conditions.

SUMMARY OF THE INVENTION

Useful photoluminescent phosphors are described in a method of detecting the presence or determining the concentration of carbon dioxide gas in a sample. The method comprises the steps of a) exposing to a predetermined wavelength range radiation a carbon dioxide-quenchable photoluminescent phosphor put in contact with said sample to cause said material to store energy radiation, b) stimulating said photoluminescent phosphor with infrared radiation to release the stored energy as photoluminescent light, c) detecting and measuring by detecting means the intensity of said photoluminescent light and d) correlating said measured intensity with an intensity of the photoluminescent light previously measured at a given reference carbon dioxide pressure value. The most useful photoluminescent phosphors are europium activated magnesium oxide phosphors having anionic vacancies.

BRIEF DESCRIPTIONS OF THE DRAWINGS

FIG. 1 shows the apparatus for the measuring of photoluminescence of stimulable phosphors.

DETAILED DESCRIPTION OF THE INVENTION

Figure 1:
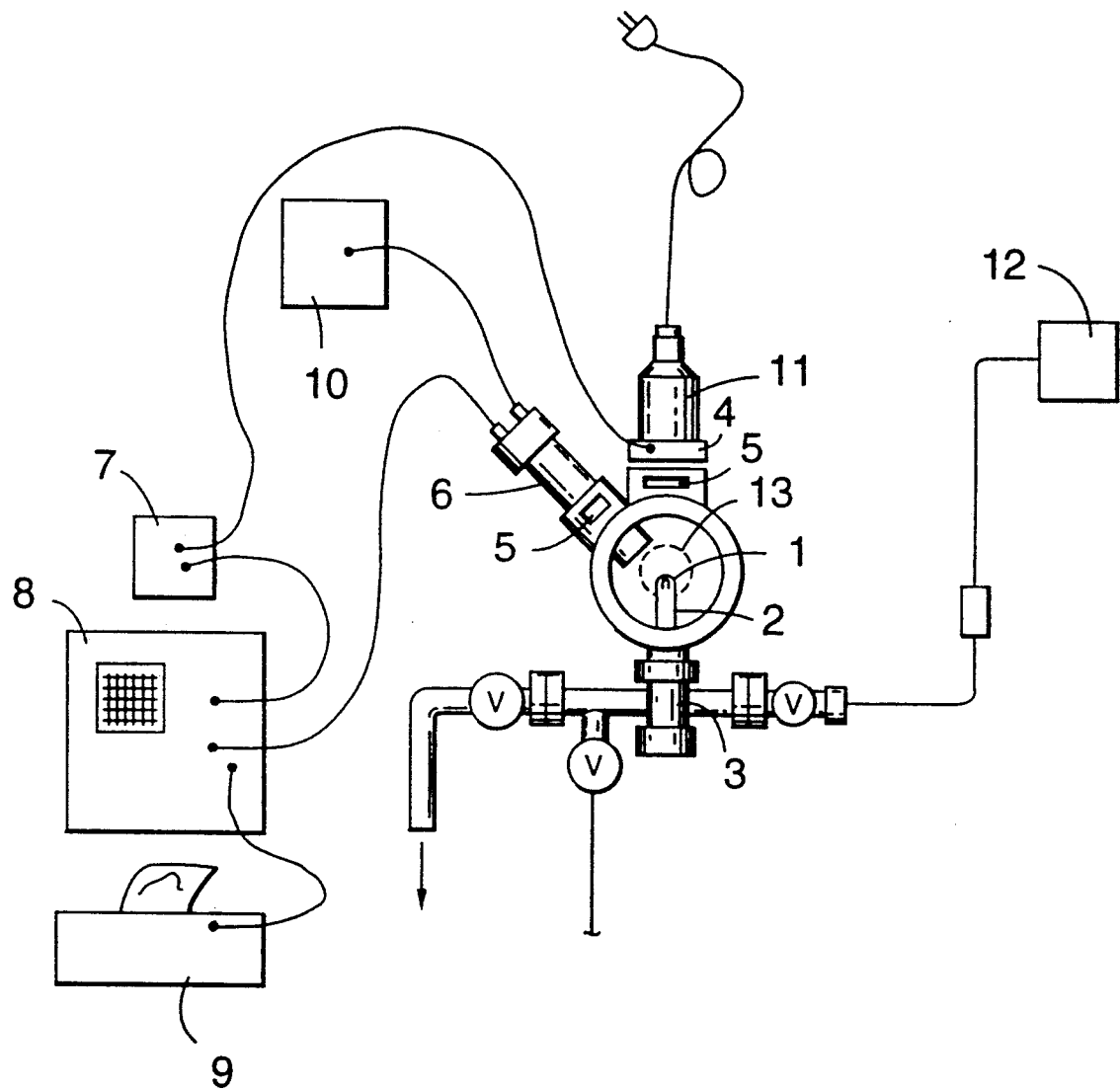

The present invention refers to a method for detecting the presence or determining the concentration of carbon dioxide gas in a sample comprising the steps of a) exposing to a predetermined wavelength range radiation a carbon dioxide-quenchable photoluminescent phosphor put in contact with said sample to cause said material to store energy radiation, b) stimulating said photoluminescent phosphor with infrared radiation to release the stored energy as photoluminescent light, c) detecting and measuring by detecting means the intensity of said photoluminescent light and d) correlating said measured intensity with an intensity of the photoluminescent light previously measured at a given reference carbon dioxide pressure value, said method being characterized by the fact that said photoluminescent phosphor is an europium activated magnesium oxide phosphor having anionic vacancies.

Preferably, the present invention refers to a method as described above wherein said sample is blood.

Preferably, said carbon dioxide-quenchable photoluminescent phosphor is $MgO:Eu^{3+}$ in a concentration range from 0.01 to 0.5 gram atoms Eu per mole MgO. More preferably, said carbon dioxide-quenchable photoluminescent phosphor is $MgO:Eu^{3+}$ in a concentration range from 0.1 to 0.3 gram atoms Eu per mole MgO.

In another aspect, the present invention refers to an apparatus for detecting the presence or determining the concentration of carbon dioxide in a sample, said apparatus comprising a) a radiation source having a predetermined wavelength range; b) a carbon dioxide-quenchable photoluminescent phosphor to be exposed by said radiation source which can store the energy of said radiation; c) an infrared stimulating radiation to cause the photoluminescent phosphor to release the stored energy as photoluminescent light; d) filtering means to filter said photoluminescent light and e) detecting means to detect and measure the intensity of said filtered photoluminescent light, characterized by the fact that said photoluminescent phosphor is an europium activated magnesium oxide phosphor having anionic vacancies.

FIG. 1 describes an apparatus for use in the present invention.

The carbon dioxide-quenchable photoluminescent phosphor (1) is enclosed in a cell (3). The exposing radiation which causes the phosphor to store energy from the exposing radiation, the stimulating radiation which causes the phosphor to release a photoluminescent radiation and said photoluminescent radiation itself are able to pass freely through at least a segment of the cell walls. In such a way, the $pCO_2$ at the carbon dioxide-quenchable and stimulable molecules interfaces is proportional to the concentration of the carbon dioxide in blood. For that reason, the suitability of a photoluminescent sensor to detect PCO2 changes can be assessed separately, in a gaseous atmosphere simulating that in equilibrium with blood.

Preferably, the predetermined wavelength radiation exposing the photoluminescent phosphor described above is in the range from 250 to 370 nm. Preferably said radiation is a UV radiation having a wavelength of 254 nm. This radiation wavelength corresponds for example to the emission of a mercury lamp 'Prolabo' of 220 V, 50 Hz, 4 Watts (11) which intensity is 250 microWatt/$cm^2$ when placed at a distance of 15 cm from the material to be exposed. The exposing radiation should generally be at an intensity of 50 to 5000 microWatt/$cm^2$.

The photoluminescent phosphor also can be excited by radiation having a wavelength longer than those previously described. In fact UV radiation sources having a wavelength of 360 nm or visible radiation sources in the regions of 400 and 500 nm can be used to excite the sensor. Radiation sources suitable for visible excitation are lasers, LEDs and lamps. For example, a Quartz-Iodine lamp of 12 V, 1100 W can be used. When said radiation sources are used, suitable interferencial optical filters (5) must be also used, such as Mellis Griot 03FIV026 and 03FIV038 types, for radiation having wavelengths, respectively, of 380–430 and 470–520 nm.

The radiation (13) stimulating the carbon dioxide-quenchable photoluminescent phosphor is an infrared radiation. Preferably, it is in the range from 700 to 1050 nm.

The carbon dioxide-quenchable photoluminescent phosphor, stimulated by said stimulating infrared radiation after being exposed to said predetermined wavelength range radiation to store energy radiation, emits a photoluminescent light in the range from 600 to 700 nm, preferably, in the range from 600 to 650 nm.

Said photoluminescent light emitted by said carbon dioxide-quenchable phosphor passes through filtering means (5). Such filtering means cut said exposing radiation and said stimulating radiation, allowing the detecting means (6) to be reached only be emitted photoluminescent radiation. According to the present invention, it is useful to use filtering means, interposed between the carbon dioxide-quenchable photoluminescent phosphor and the detecting means (6), and having a transmittance in the range from 595 to 650 nm, such as a Melles Griot 03FIB-012 filter type.

Said filtered emitted photoluminescent radiation is detected by detecting means such as a grating monochromator (for example a Grate Oriel 7271 type) and a photomultiplier (6), for example a Thorn Emi 9658 RA type. The data may be elaborated upon by a Data 6000 Analyzer Mod. 620 Data Precision (8) and are then printed using a printing unit (9).

The photoluminescent materials of the present invention are prepared by dissolving magnesium oxide and europium oxide in diluted nitric acid. The solution is evaporated in air and dried till complete evolution of the red nitrogen dioxide. The product is subsequently fired in air, as in an alumina crucible. The obtained solid solution is subjected to a second firing in slowly reducing atmosphere, i.e. by using a mixture of $N_2+H_2$ (5% $H_2$), or by putting carbon between the reaction crucible and a second layer, covered by an alumina cover. After cooling, the product is sieved, in presence of ethyl alcohol and dried. The product has the appearance of a white crystalline powder; it is then stored in a container subject to moderate vacuum.

That preparation process, performed in a reducing atmosphere, rather than in an oxygen rich atmosphere, allows the magnesium oxide phosphors of the present invention to be photoluminescent phosphors suitable for carbon dioxide adsorption. The magnesium oxide phosphors emit photoluminescent radiations, when exposed to a predetermined wavelength radiation which causes the phosphor to store energy to be released upon stimulation by infrared stimulating radiations. This property is the consequence of the formation of anionic vacancies in the bulk and on the surface of the magnesium oxide phosphors obtained by the preparation process previously described. The anionic vacancies represent atomic defects in the structure of magnesium oxide phosphors; they are oxygen vacancies situated at intermediate energy levels between the conduction and the valence bands of magnesium oxide. (see Rosenblatt G. H. et all, *Physical Review* B, Vol. 39, No. 14, pp 10309-10318). The anionic vacancies can also be obtained using other techniques different from the preparation process described above. For example, anionic vacancies can be also obtained by irradiating the oxides, possibly in a vacuum, with ionizing radiations, such as gamma, X-ray and UV radiations, or by doping the oxides with alkaline metals or with an excess of magnesium metal.

Other magnesium oxide compounds, different from the ones described in the present invention, that do not show said anionic vacancies are not useful for the purpose of this invention as such vacancies constitute the main surface carbon dioxide adsorption sites.

The measurements are carried out in a cell (3) like that shown in FIG. 1. The standard experimental routine involves the evacuation of the cell for about 20 hours at room temperature (preconditioning of the sensor). That procedure allows a minimum quantity of humidity in the cell. After that evacuation, dry $N_2$ is introduced in the cell in order to establish a clean atmosphere at normal pressure. A first measurement of the intensity of the radiation emitted by the carbon dioxide-quenchable photoluminescent phosphor is performed at a reference $pCO_2$ value of 15 Torr, using mixture of $CO_2+N_2$ with controlled composition. Establishing a constant low flux of introduction of gas at successively higher carbon-dioxide partial pressure values and measuring each time the related intensity of the radiation emitted by the carbon dioxide-quenchable photoluminescent phosphor, provides a range of values related to the quantity of carbon dioxide present in the cell. There is a reverse proportional relationship between the intensity of the emitted photoluminescent radiation measured in presence of carbon dioxide gas and the concentration of carbon dioxide gas present in the sample: the greater the measured intensity, the lower is the carbon dioxide concentration. In fact, the phosphor exposition to UV radiation causes the formation of electron hole pairs which migrate until the electrons are captured by the oxygen defects present in the photoluminescent phosphor: in the presence of small amounts of carbon dioxide in the cell, the infrared stimulation causes the release of the electrons captured by said oxygen defects, permitting the recombination of the electron hole pairs. In this way the photoluminescent phosphor emits a photoluminescent radiation. On the contrary, the presence of carbon dioxide in the cell in sufficiently high amounts causes the carbon dioxide adsorption on the surface of the grains of the carbon dioxide-quenchable photoluminescent phosphor. This carbon dioxide adsorption traps part of the electrons which are not allowed in this case, when stimulated by the infrared radiation, to recombine with the holes: in this case there is only a partial emission of the photoluminescent radiation. Finally, when there is a very large amount of carbon dioxide in the cell, all the electrons are practically trapped by the carbon dioxide adsorption: in this case there is almost no photoluminescent radiation emitted by the carbon dioxide-quenchable photoluminescent phosphor.

To determine the amount of carbon dioxide gas present in the sample, for example in blood, the measured intensity of said photoluminescent radiation emitted by the carbon dioxide-quenchable photoluminescent phosphor of the present invention, when exposed to a predetermined wavelength radiation and successively stimulated by an infrared radiation, is then correlated with the reference intensity values previously measured.

The photoluminescent sensor is constituted by a coating of the photoluminescent compound prepared according the preparation process described above and a binder. The binders may be those commonly used for the formation of layers, such as organic polymeric binders, such as polyvinylbutyral, polyvinylacetate, nitrocellulose, ethylcellulose, vinylidenechloride-vinylchloride copolymers, acrylic polymers such as polymethylmethacrylate and polybutylmethacrylate, vinylchloride-vinylacetate copolymers, polyurethane, cellulose acetate-butyrate and the like.

In general, the binder is used in a quantity ranging from 0.01 to 1 part by weight per each part by weight of the photoluminescent material. However, with respect to the sensitivity of the obtained sensor, the binder quantity should preferably be small, in a range from 0.05 to 0.5 part by weight per each part by weight of the photoluminescent material. The binder is also preferably not soluble in liquids into which it is to come into contact during use.

The photoluminescent sensor can be also constituted by a coating of the photoluminescent phosphor prepared according the preparation process described above without the use of a binder. Thin binderless layers, as prepared by well known different techniques such as: spray pyrolisis, chemical vapour deposition, sputtering, reactive evaporation, powder sintering, epitaxy, electrochemical deposition and the like, can be particularly suitable to get photoluminescent sensors. This technique works well when the surface to bulk ratio is high. This can be realized by minimizing the thickness of the layer or increasing the porosity of the surface. Such techniques are particularly advantageous in producing small area photoluminescent sensors.

The photoluminescent layer (1) is assembled at the top of a cylindrical steel support, as a coated layer having a thickness in the range from 10 micrometers to 1 mm. After coating, the steel support is immediately put in a furnace and there maintained to lose rapidly solvents and acquire porosity, when organic binders are used. After cooling, the sensor can be stored in a dry atmosphere, possibly under slowly reduced pressure.

EXAMPLES

EXAMPLE 1

Preparation of $MgO:Eu^{3+}$ at a Concentration of 0.15 Grams Atoms Eu per Mole MgO 4.9936 grams of 99% MgO and 0.0218 grams of 99,99% $Eu_2O_3$ were dissolved in 150 $cm^3$ of $HNO_3$ (65%). The solution was evaporated at 100° C. in air and dried till complete evolution of the red nitrogen dioxide. The product was subsequently fired for two hours in air, in an alumina crucible, at 1000° C. The obtained solid solution of $Eu_2O_3$ in MgO was then subjected, in the same manner, to a second firing at 1000° C. for 1 hour in slowly reducing atmosphere by putting carbon between the reaction crucible and a second layer, covered by an alumina cover. After cooling, the product was sieved, in the presence of ethyl alcohol, by using a 30 mesh nylon net and dried at 100° C. The product had the appearance of a white crystalline powder; it has been stored in a container subject to moderate vacuum.

EXAMPLE 2

Measurements of Photoluminescence Intensity Response to $pCO_2$ Changes

The photoluminescent sensor comprised a coating of the photoluminescent compound prepared according to Example 1 and a polymeric organic binder at a 3:1 weight ratio of compound to binder. As shown in FIG. 1, the phosphor sensor (1) has been assembled at the top of a cylindrical steel support, as a coated layer having a thickness of 100 micrometers. After coating, the steel support has been immediately put in a furnace at 130° C. and there maintained for half an hour to rapidly lose solvents and acquire porosity.

Measurements have been carried out in the cell (3) shown in FIG. 1. The standard experimental routine involved the evacuation of the cell (3) for about 20 hours at room temperature (preconditioning of the sensor). After that evacuation, dry $N_2$ was introduced in the cell in order to establish a clean atmosphere at normal pressure. A first measurement of photoluminescence intensity could be performed at a reference $pCO_2$ value of 15 Torr. Further values of intensity at the various pCO₂ values have been measured by using N₂+CO₂ gas mixtures (12). Table 1 reports values of the intensity of the photoluminescence as measured by the photomultiplier (6), expressed in mV, at the various pCO₂ levels. It must be noted that the actual intensity values depend on the employed experimental assembly, exciting source power, optical accessories and the like.

An o-ring assured a sufficiently tight interface between the sensor support base and the external structure of the cell. At the opposite side, a quartz cup (2) fixed to the external steel structure with an epoxy resin, assured the optical transmission of the exposing radiation, of the infrared stimulating radiation and of the released radiation upon stimulation in the complete spectral range of interest (250-1000 nm).

A conventional mercury lamp (11) having a wavelength of 254 nm has been used as radiation source. It was a "Prolabo" mercury lamp of 220 V, 50 Hz, 4 Watts, which intensity was of 250 milliWatt/cm² when placed at a distance of 15 cm from the material to be exposed. As shown in FIG. 1, an electronic shutter (4) driven by a time selector (7) permitted to optically connect the excitating radiation source (11) with the sensor (1), through the quartz cover (2).

The carbon dioxide-quenchable photoluminescent phosphor stored the energy radiation corresponding to said excitating radiation. Then the phosphor was stimulated by an infrared stimulating radiation (13) having a wavelength of 750 nm, corresponding to the emission of a standard Quartz-Iodine lamp. The radiation flux, modulated by an electronic shutter, was incident on the quartz head at 0.007 milliWatt/cm².

Upon said infrared stimulation, the MgO:Eu³⁺ phosphor had a photoluminescent emission in the red-near IR range with a peak at 615 nm. Said emitted radiation passed through an interferencial optical filter Melles Griot 03FIB-012 (5) having a transmittance window of about 60% in the range 545-640 nm. The filter (5) was interposed between the cell (3) and the photomultiplier Thorn EMI, type 9658 RA (6). The intensity of the photoluminescence emitted by the stimulated phosphor (1), through the multiplier (6), was read by the Data 6000 Analyzer Mod. 620 Data Precision (8) one second after starting stimulation. Then, the electronic shutter (4) was immediately closed. This method reduced to a minimum the damage of the sensor, due to formation of color centers and to saturation effects due to full occupancy of surface adsorption sites.

Luminescent spectra were obtained by using a grating monocromator (Grate Oriel 7271) connected to the photomultiplier (6), visualized on the Data 6000 Analyzer and recorded by a Hewlett Packard Plotter (9).

TABLE 1

| CO₂ pressure TORR | Relative Photoluminescence Intensity (nm) | | | | | |
|---|---|---|---|---|---|---|
| | 470 | 700 | 800 | 900 | 1000 | 1100 |
| 15 | 1.00 | 1.00 | 1.00 | 1.00 | 1.00 | 1.00 |
| 80 | 1.05 | 1.00 | 0.90 | 0.68 | 0.82 | 1.34 |
| 150 | 1.13 | 1.00 | 0.70 | 0.45 | 0.52 | 1.70 |

In Table 1, the photoluminescence intensity values concerning pCO₂ at 15, 80 and 150 Torr, measured according to the previously described procedure, are reported, when the phosphor was stimulated by radiation having wavelengths in the range 470-1100 nm. We have used as a reference value 1.00 the signal intensity value when the pCO₂ is 15 Torr. Data are given as ratio between the signal intensity value at the measured pCO₂ and the reference value.

A more detailed range of photoluminescence intensity values, according to different carbon dioxide pressures, can be obtained. Once more detailed values have been obtained, it is easy to determine the carbon dioxide pressure in the blood. In fact, it is sufficient to measure the photoluminescent intensity value in the presence of a blood sample and to compare it with the data of the table of photoluminescent intensity values previously measured. The quantity of carbon dioxide pressure is thus immediately obtained.

It appears from the data reported in Table 1 that, when the phosphor was stimulated by stimulating radiation having a wavelength of 700 nm, the intensity values measured at a pCO₂ values of 80 and 150 Torr were equal to the reference value related to pCO₂ of 15 Torr. That means that, when stimulated at 700 nm, the phosphor used in the present invention is not useful to detect the concentration of carbon dioxide partial pressure in the blood.

On the contrary, when the phosphor was stimulated by stimulating radiation having wavelength of 800, 900, 1000, the data shown in Table 1 confirm the possibility of detecting the carbon dioxide partial pressure in the blood.

Furthermore, when stimulated by a low or by a very high wavelength radiation, respectively at 470 and 1100 nm, it appears that measured intensity values are increasing at higher pCO₂ levels rather than decreasing: there is an inversion of tendency. This fact indicates that the phosphor of the present invention is not as useful to detect the pCO₂ when stimulated at said wavelength values.

I claim:

1. Method for detecting the presence or determining the concentration of carbon dioxide gas in a sample comprising the steps of a) exposing to a predetermined wavelength range radiation a carbon dioxide-quenchable photoluminescent phosphor put in contact with said sample to cause said phosphor to store radiation, b) stimulating said photoluminescent phosphor with infrared radiation to release the stored energy as photoluminescent light, c) detecting and measuring by detecting means the intensity of said photoluminescent light and d) correlating said measured intensity with an intensity of the photoluminescent light previously measured at a given reference carbon dioxide pressure value, wherein said photoluminescent phosphor is an europium activated magnesium oxide phosphor having anionic vacancies.

2. Method for detecting the presence or determining the concentration of carbon dioxide gas in a sample of claim 1 wherein said sample is blood.

3. Method for detecting the presence or determining the concentration of carbon dioxide gas in a sample of claim 1 wherein said photoluminescent phosphor is MgO:xEu³⁺, wherein x is in the range from 0.01 to 0.5 gram atoms per mole of MgO.

4. Method for detecting the presence or determining the concentration of carbon dioxide gas in a sample of claim 1 wherein said photoluminescent phosphor is MgO:xEu³⁺, wherein x is in the range from 0.1 to 0.3 grams atoms per mole of MgO.

5. Method for detecting the presence or determining the concentration of carbon dioxide gas in a sample of claim 1 wherein said predetermined wavelength radiation exposing the photoluminescent phosphor is in the range from 250 to 370 nm.

6. Method for detecting the presence or determining the concentration of carbon dioxide gas in a sample of claim 1 wherein said infrared radiation stimulating said photoluminescent phosphor is in the range from 700 to 1050 nm.

* * * * *